United States Patent

Zeiss et al.

[11] Patent Number: 4,692,541
[45] Date of Patent: Sep. 8, 1987

[54] PHOSPHORUS-CONTAINING α-AMINO NITRILES AND A PROCESS FOR THEIR PREPARATION

[75] Inventors: Hans-Joachim Zeiss, Sulzbach; Hilmar Mildenberger, Kelkheim, both of Fed. Rep. of Germany

[73] Assignee: Hoechst Aktiengesellschaft, Frankfurt am Main, Fed. Rep. of Germany

[21] Appl. No.: 837,721

[22] Filed: Mar. 7, 1986

[30] Foreign Application Priority Data

Mar. 11, 1985 [DE] Fed. Rep. of Germany ....... 3508573

[51] Int. Cl.$^4$ ............................. C07F 9/32; C07F 9/50
[52] U.S. Cl. ..................................... 558/87; 558/167; 558/386
[58] Field of Search .......................... 558/167, 87, 386

[56] References Cited

U.S. PATENT DOCUMENTS 4,168,963 9/1979 Rupp et al. ............................. 71/86

FOREIGN PATENT DOCUMENTS 2717440 4/1977 Fed. Rep. of Germany .

OTHER PUBLICATIONS

Zeiss et al, "Chemical Abstracts," vol. 105, (1986) 227009.

H. Geipel et al., "Eine einfache Synthese fur β-Hydroxy-γ-α-aminosauren," Jahrg. 98, pp. 1677–1680 (1965).

Primary Examiner—Anton H. Sutto
Attorney, Agent, or Firm—Curtis, Morris & Safford

[57] ABSTRACT

A process for the preparation of phosphorus-containing α-amino nitriles of the general formula I

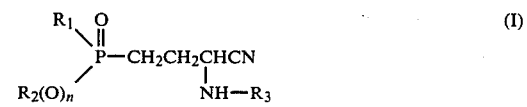

in which $R_1$ and $R_2$ denote (substituted) alkyl, aryl, aralkyl or cycloalkyl, $R_3$ denotes H, alkyl, phenalkyl, acyl, alkoxycarbonyl or aryloxycarbonyl, and n denotes zero or one, by reaction of corresponding acylals with alkali metal cyanides under the conditions of the Strecker synthesis.

23 Claims, No Drawings

PHOSPHORUS-CONTAINING α-AMINO NITRILES AND A PROCESS FOR THEIR PREPARATION

The present invention relates to new, phosphorus-containing α-amino nitriles of the general formula I

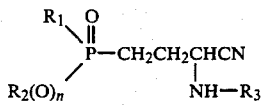

in which $R_1$ denotes $(C_1-C_6)$-alkyl which can be substituted once or several times by halogen or alkoxycarbonyl, or denotes $(C_6-C_{10})$-aryl, $(C_7-C_{10})$-aralkyl or $(C_3-C_{10})$-cycloalkyl, $R_2$ denotes $(C_1-C_6)$-alkyl which can be substituted once or several times by halogen, or denotes $(C_6-C_{10})$-aryl, $(C_7-C_{10})$-aralkyl or $(C_3-C_{10})$-cycloalkyl, $R_3$ denotes hydrogen, $(C_1-C_6)$-alkyl or -phenalkyl, $(C_1-C_6)$-acyl, $(C_1-C_6)$-alkoxycarbonyl or $(C_6-C_{10})$-aryloxycarbonyl, and n denotes zero or one.

The invention also relates to a process for the preparation of compounds of the formula I, which comprises reaction of compounds of the general formula II

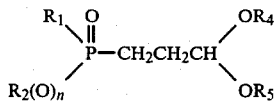

in which $R_4$ and $R_5$, independently of one another, denote $(C_1-C_6)$-acyl, $(C_1-C_6)$-alkoxycarbonyl, phenoxycarbonyl or napththoxycarbonyl, in the presence of alkali metal cyanides, with amines of the general formula III

and, if desired, elimination, by known methods, of a radical $R_3$ which is not hydrogen from the resulting compounds of the formula I.

$R_1$ in the compounds of the formula II preferably denotes lower alkyl, in particular methyl or ethyl. "Aryl" preferably represents the phenyl radical, and "aralkyl" preferably represents the benzyl radical. Cycloalkyl is to be understood to include, in particular, cyclopropyl, cyclopentyl and cyclohexyl. $R_2$ preferably denotes lower alkyl, and $R_4$ and $R_5$ preferably denote acetyl, methoxycarbonyl or ethoxycarbonyl.

$R_3$ in the amines of the formula III preferably denotes hydrogen or $(C_1-C_2)$-alkoxycarbonyl.

The elimination of radicals $R_3$ which are not hydrogen from the products obtained in the 1st stage of the process is carried out by known methods familiar to those skilled in the art, for example by catalytic hydrogenation or hydrolysis.

If, for example, $R_3$ is a radical which contains a center of chirality (for example 1-phenylethyl), then the process according to the invention can be used for the preparation of optically active phosphorus-containing α-amino nitriles. This entails the chirality being carried over from $R_3$ to the carbon atom adjacent to the CN group (cf. Tetrahedron 39, 1299 (1983)). It is then possible, by hydrogenation with Pd catalysis, to eliminate the radical $R_3$ from the resulting compounds with $R_3$ in which $R_3$ is not hydrogen and thus obtain optically active compounds in which $R_3$ is hydrogen.

Compounds of the formula II can be prepared straightforwardly by known processes.

Thus, for example in German Offenlegungsschrift No. 2,516,343, the preparation of compounds of the formula II by addition of phosphorus-hydrogen compounds onto diacylates of unsaturated aldehydes is described.

The process according to the invention is generally carried out such that compounds of the general formula II are allowed to react with amines of the general formula III, in aqueous reaction solution and in the presence of alkali metal cyanides, in particular those of potassium and of sodium, and then the resulting product of the general formula I is extracted with a solvent which is immiscible with water.

The alkali metal cyanides are used in amounts of 90–120 mol-%, but preferably in equimolar amounts, relative to the component of the general formula II.

The process is advantageously carried out in the pH range 8–12. Thus, when strongly basic starting materials of the formula III are used, it is necessary to carry it out in buffered solution. The buffer systems used are those which do not intervene in the reaction, for example the system $HPO_4^-/PO_4^{2-}$. Other suitable buffer systems are known to those skilled in the art and do not need to be listed specifically.

For example, in the case where ammonia is used as the amine component (general formula III: $R_3=H$), the pH of the reaction solution is adjusted to between 8 and 12, preferably between 9.0 and 10.8, by addition of ammonium chloride.

The compounds of the formula III are used in at least equimolar amounts, but preferably in excess.

The process according to the invention is carried out at reaction temperatures of 0°–100° C., preferably 25°–45° C.

The reaction time is 0.3–24 h, preferably 0.6–8 h.

It is surprising that it is possible to convert the readily accessible acylal derivatives of the formula II, in place of the aldehydes from which they are derived and which are not readily accessible, into α-amino nitriles of the formula I under the conditions of the Strecker synthesis. This is all the more the case since aldehyde derivatives which contain the acetal structure

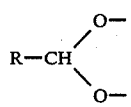

are known to be substantially chemically inert under basic reaction conditions, as prevail in the Strecker synthesis, and reactions at the masked aldehyde group normally take place only under acid reacton conditions. Although α-amino nitriles have been postulated as intermediates in the preparation of non-phosphorus-containing amino acids from aldehyde acylals, nevertheless their isolation has not been described, and the yields of the amino acids vary greatly, depending on the substituent (Ber. 98, 1677 (1965)). In contrast, the process according to the invention allows the preparation of phosphorus-containing α-amino nitriles of the general formula I in virtually quantitative yields.

α-Amino nitriles of the general formula I are valuable precursors, since they can be hydrolyzed, by processes known from the literature (Houben-Weyl XI/2, page 305 and page 371, G. Thieme, Stuttgart 1958) both in acid and in alkaline media, to give biologically active amino acids, which have bactericidal (Helv. Chim. Acta 55,224 (1972)), fungicidal (Sci. Rep. Meiji Seika Kaisha 13, 34 (1973)) and herbicidal actions (German Offenlegungsschrift 2,717,440). Thus, for example, hydrolysis of the examples which follow results in the compound 3-methylphosphinoyl-1-aminobutyric acid, which has outstanding herbicidal properties (German Offenlegungsschrift No. 2,717,440).

The examples which follow are intended to illustrate the process in detail but without thereby intending any restriction.

EXAMPLE 1

2-Amino-4-(2-methylpropoxy(methyl)phosphinoyl)-butyronitrile 14.70 g (0.05 mol) of 3,3-diacetoxy-1-(2-methylpropoxy-(methyl)phosphinoyl)propane, 5.30 g (0.1 mol) of ammonium chloide and 2.45 g (0.05 mol) of sodium cyanide are dissolved in 60 ml of concentrated ammonia (about 25% strength), during which the temperature rises to 40° C. The reaction mixture is stirred at room temperature for 6 h. The pH rises from 9.4 at the start to 10.4 towards the end of the reaction. The aqueous reaction mixture is extracted 3 times with 100 ml of dichloromethane each time, and the organic extracts are combined, dried over $Na_2SO_4$ and evaporated. Solvent residues are removed under high vacuum at room temperature.

10.9 g (100% of theory) of 2-amino-4-(2-methylpropoxy-(methyl)phosphinoyl)butyronitrile are obtained as a colorless oil.

$^1$H-NMR (CDCl$_3$): 0.90 (d, J=6 Hz, 6H), 1.43 (d, J=14 Hz, 3H) overlapped by 1.00–2.60 (m, 7H), 3.70 (t, J=7 Hz, 3H).

IR (film): 895, 1025, 1205, 1300, 1475, 1620, 2230, 2870, 2960, 3290, 3370.

R$_f$ values:

precoated silica gel plates (Merck); mobile phase; toluene/ethyl acetate/n-butanol 1:1:1.

Product 0.16.

Starting material 0.48.

$C_9H_{19}N_2O_2P$ (218.24) Calculated C 49.5 H 8.8 N 12.8. Found C 49.1 H 8.7 N 12.0.

EXAMPLE 2

2-Amino-4-(3-methylbutoxy(methyl)phosphinoyl)-butyronitrile 29.28 g (0.095 mol) of 3,3-diacetoxy-1-(3-methylbutoxy-(methyl)phosphinoyl)propane, 10.20 g (0.19 mol) of ammonium chloride and 4.65 g (0.095 mol) of sodium cyanide are dissolved in 120 ml of concentrated ammonia (about 25% strength), during which the temperature rises to 40° C. The reaction mixture is stirred at room temperature for 1 h. The pH rises from 9.8 at the start to 10.4 towards the end of the reaction. The aqueous reaction mixture is extracted 3 times with 100 ml of dichloromethane each time, and the organic extracts are combined, dried over $Na_2SO_4$ and evaporated. Solvent residues are removed under high vacuum at room temperature.

21.4 g (97.1% of theory) of 2-amino-4-(3-methylbutoxy-(methyl)phosphinoyl)butyronitrile are obtained as a colorless oil.

$^1$H-NMR (CDCl$_3$): 0.92 (d, J=6 Hz, 6H), 1.48 (d, J=14 Hz, 3H), overlapped by 1.40–2.10 (m, 9H), 3.84 (t, J=6 Hz, 1H) partially overlapped by 4.00 (q, J=7 Hz, 2H)

IR (film): 905, 990, 1015, 1060, 1205, 1305, 1480, 1625, 2230, 2870, 2930, 2960, 3290, 3370.

R$_f$ values:

precoated silica gel plates (Merck); mobile phase: n-butanol/glacial acetic acid/water 5:2:2.

Product: 0.58.

Starting material: 0.69.

$C_{10}H_{21}N_2O_2P$ (232.26) Calculated C 51.7 H 9.1 N 12.1. Found C 51.4 H 9.2 N 11.1.

The starting compound of Example 1 is obtained as follows:

3,3-Diacetoxy-1-(2-methylpropoxy(methyl)phosphinoyl)propane 202 g (1.49 mol) of mono-2-methylpropyl methanephosphonite are heated to 110° C. and, under nitrogen, a mixture of 156 g (0.99 mol) of 3,3-diacetoxy-1-propene (prepared by reaction of acrolein with acetic anhydride) and 4.7 g (0.022 mol) of t-butyl peroctoate is added. After addition is complete (1 h), stirring is continued for a further 1 h. Excess mono-2-methylpropyl methanephosphonite is removed first under waterpump vacuum and then under high vacuum. 306.2 g (92.9%) of 3,3-diacetoxy-1-(2-methylpropoxy(methyl)phosphinoyl)propane remain as the residue.

We claim:

1. A process for the preparation of a compound of the formula I

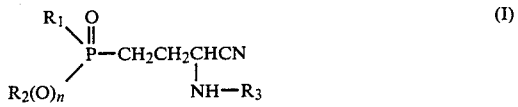

in which
R$_1$ is (C$_1$–C$_6$)-alkyl which is unsubstituted, monosubstituted or polysubstituted by halogen or by alkoxycarbonyl, or is (C$_6$–C$_{10}$)-aryl, (C$_7$–C$_{10}$)-aralkyl, or (C$_3$–C$_{10}$)-cycloalkyl, R$_2$ is (C$_1$–C$_6$)-alkyl which is unsubstituted, monosubstituted or polysubstituted by halogen, or is (C$_6$–C$_{10}$)-aryl, (C$_7$–C$_{10}$)-aralkyl, or (C$_3$–C$_{10}$)-cycloalkyl, R$_3$ is hydrogen, (C$_1$–C$_6$)-alkyl or -phenalkyl, (C$_1$–C$_6$)-acyl, (C$_1$–C$_6$)-alkoxycarbonyl, or (C$_6$–C$_{10}$)-aryloxycarbonyl, and n is zero or one, which comprises reacting a compound of the formula II

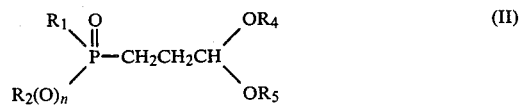

in which R$_4$ and R$_5$, independently of one another, are (C$_1$–C$_6$)-acyl, (C$_1$–C$_6$)-alkoxycarbonyl, phenoxycarbonyl or naphthoxycarbonyl, in the presence of alkali metal cyanides, with amines of the formula III

H₂H—R₃  (III).

2. The process as claimed in claim 1, which further comprises reacting the compound of formula II and the compound of formula III in an aqueous reaction medium.

3. The process as claimed in claim 1, which further comprises adjusting the pH of the reaction mixture of the compound of formula II and the compound of formula III to 8 to 12.

4. The process as claimed in claim 3, wherein ammonium chloride is used to adjust the pH of the reaction mixture.

5. The process or claimed in claim 1 in which $R_1$ is ($C_1$–$C_6$) alkyl, phenyl, benzyl, cyclopropyl, cyclopentyl or cyclohexyl, $R_2$ is ($C_1$–$C_6$) alkyl, $R_3$ is hydrogen or ($C_1$–$C_2$) alkoxycarbonyl, and $R_4$ and $R_5$, independently of one another, are acetyl, mehoxycarbonyl or ethoxycarbonyl.

6. The process as claimed in claim 1 in which the compound of the formula II and the compound of the formula III are reactred in an aqueous reaction medium at a pH between 8 and 12 in the presence of an alkali metal cyanide and the resulting product of the formula I is extracted with a solvent which is immiscible with water.

7. The process as claimed in claim 1 further comprising elimination of the radical $R_3$ from the compound of formula I when $R_3$ is other than hydrogen.

8. The process as claimed in claim 4, wherein the pH of the reaction mixture is adjusted to 9.0 to 10.8.

9. The process as claimed in claim 1, wherein the alkali metal cyanide is used in amount of 90–120 mol %.

10. The process as claimed in claim 1, wherein the alkali metal cyanide is used in equimolar amount relative to the amount of the compound of formula III.

11. The process as claimed in claim 1, wherein the alkali metal cyanide is potassium cyanide or sodium cyanide.

12. The process as claimed in claim 1, which further comprises reacting the compound of formula II and the compound of formula III in equimolar amounts.

13. The process as claimed in claim 1, wherein the compound of formula III is used in excess.

14. The process as claimed in claim 1, which further comprises reacting the compound of formula II and the compound of formula III at a temperature of 0° to 100° C.

15. The process as claimed in claim 14, wherein the reaction is carried out at a temperature of 25° to 45° C.

16. The process as claimed in claim 1, which further comprises reacting the compound of formula II and the compound of formula III for a time of 0.3 to 24 hours.

17. The process as claimed in claim 16, wherein the reaction is carried out for a time of 0.6 to 8 hours.

18. a compound of the formula I

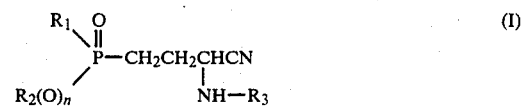

in which $R_1$ is ($C_1$–$C_6$)-alkyl which is unsubstituted, monosubstituted or polysubstituted by halogen or by alkoxycarbonyl, or is ($C_6$–$C_{10}$)-aryl, ($C_7$–$C_{10}$)-aralkyl, or ($C_3$–$C_{10}$)-cycloalkyl, $R_2$ is ($C_1$–$C_6$)-alkyl which is unsubstituted, monosubstituted or polysubstituted by halogen, or is ($C_6$–$C_{10}$)-aryl, ($C_7$–$C_{10}$)-aralkyl, or ($C_3$–$C_{10}$)-cycloalkyl, $R_3$ is hydrogen, ($C_1$–$C_6$)-alkyl or -phenalkyl, ($C_1$–$C_6$)-acyl, ($C_1$–$C_6$)-alkoxycarbonyl, or ($C_6$–$C_{10}$)-aryloxycarbonyl, and n is zero or one.

19. The compound as claimed in claim 18 in which $R_1$ is methyl, $R_2$ is 2-methylpropyl or 3-methylbutyl, $R_3$ is hydrogen and n is 1.

20. The compound a claimed in claim 18, in which $R_1$ is ($C_1$–$C_6$) alkyl, phenyl, benzyl, cyclopropyl, cyclopentyl or cyclohexyl.

21. The compound as claimed in claim 18, in which $R_2$ is ($C_1$–$C_6$) alkyl.

22. The compound as claimed in claim 18, in which $R_4$ and $R_5$, independent of each other, are acetyl, methoxycarbonyl or ethoxycarbonyl.

23. The compound as claimed in claim 18 in which $R_3$ is hydrogen or ($C_1$–$C_2$) alkoxycarbonyl.

* * * * *